(12) United States Patent
Bao et al.

(10) Patent No.: US 7,863,603 B1
(45) Date of Patent: Jan. 4, 2011

(54) CROSS-LINKED ORGANIC THIN-FILM DIELECTRICS

(75) Inventors: Zhenan Bao, Stanford, CA (US); Mark E. Roberts, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 408 days.

(21) Appl. No.: 11/781,725

(22) Filed: Jul. 23, 2007

Related U.S. Application Data

(60) Provisional application No. 60/832,838, filed on Jul. 24, 2006.

(51) Int. Cl.
*H01L 35/24* (2006.01)
(52) U.S. Cl. .................. 257/40; 257/595; 525/328.8
(58) Field of Classification Search ............ 257/40, 257/E29.242, 595; 438/99; 525/328.8
See application file for complete search history.

(56) References Cited

U.S. PATENT DOCUMENTS 7,605,392 B2 * 10/2009 Nakayama et al. ............ 257/40

OTHER PUBLICATIONS

Klauk et al. (Journal of Applied Physics, 92(9), 2002, 5259-5263).*
Yoon et al. *Low-Voltage Organic Field-Effect Transistors and Inverters Enabled by Ultrathin Cross-Linked Polymers as Gate Dielectrics*, J. Am. Chem. Soc., 2005, 127, 10388-10395.
Someya et al., *Integration and Response of Organic Electronics with Aqueous Microfluidics*, Langmuir, 2002, 18, 5299-5302.
Facchetti et al. *Gate Dielectrics for Organic Field-Effect Transistors: New Opportunities for Organic Electronics*, Adv. Mater., 2005, 17, 1705-1725.
Schroeder et al. *High-Performance Organic Transistors Using Solution-Processed Nanoparticle-Filled High-k Polymer Gate Insulators*, Adv. Mater., 2005, 17, 1535-1539.
Chen et al. *Organic thin-film transistors with nanocomposite dielectric gate insulator*, Applied Physics Letters, 2004, Col. 85, No. 15.

* cited by examiner

*Primary Examiner*—David Wu
*Assistant Examiner*—Vu A Nguyen
(74) *Attorney, Agent, or Firm*—Crawford Maunu PLLC

(57) ABSTRACT

Cross-linked dielectric layers are facilitated. According to an example embodiment, an organic polymer is mixed with a reaction-stabilized cross-linking material. The organic polymer is cross-linked with the reaction-stabilized cross-linking material to form a dielectric layer.

19 Claims, 6 Drawing Sheets

CROSS-LINKED ORGANIC THIN-FILM DIELECTRICS

RELATED PATENT DOCUMENTS

This patent document claims the benefit, under 35 U.S.C. §119(e), of U.S. Provisional Patent Application No. 60/832,838 filed Jul. 24, 2006, entitled: "Cross-Linked Organic Thin-Film Dielectrics" and which is fully incorporated herein by reference.

FEDERALLY-SPONSORED RESEARCH OR DEVELOPMENT

This invention was made with Government support under contract 0213618 awarded by the National Science Foundation. The U.S. Government has certain rights in this invention.

FIELD OF THE INVENTION

The present invention relates generally to semiconductor devices, and more particularly to arrangements and approaches involving organic thin-film dielectrics.

BACKGROUND

Semiconductor device applications have experienced significant scaling (reduction in size) over recent years, with continued scaling desirable for a multitude of applications. In addition, semiconductors and semiconductor devices are increasingly used in cross-disciplinary applications, in various configurations, and in unique operating environments.

A number of semiconductor device applications involve organic thin films, such as those implemented with organic thin-film transistors (OTFT, or OTFTs), capacitors and other devices. These devices have shown usefulness in a variety of applications. For instance, OTFTs are useful for performing a variety of functions and offer unique characteristics desirable for many applications. See, e.g., Sze, S. M. *Semiconductor Devices: Physics and Technology*, 2nd edition; Wiley: New York, 1981. Generally, these devices are low in weight, flexible in application, inexpensive and useful for a multitude of applications.

While organic semiconductor devices are useful for many applications, their manufacture and implementation has been challenging. For instance, many applications directed to the formation of OTFTs require relatively high temperature (e.g., over 150° C., or over 200° C.). Such high temperature can be challenging to implement with certain materials. The formation of organic thin film layers of desirable form and arrangement has also been challenging; many applications are subject to the formation of dielectric layers having undesirable characteristics such as pinholes. Other challenges to the formation of organic thin film devices relate to processing characteristics, including those related to the ease, consistency and quality of the manufacture of dielectric layers. For instance, many manufacturing approaches have been characterized by undesirable moisture sensitivity, high reactivity, and rough surfaces. Still other challenges to the implementation of organic thin film devices are related to compatibility with different gate and channel materials, and with organic semiconductors.

These and other characteristics have been challenging to the design, manufacture and use of semiconductor devices, and in particular, of dielectric materials for organic thin-film semiconductor devices used in both aqueous and non-aqueous environments.

SUMMARY OF THE INVENTION

The present invention is directed to overcoming the above-mentioned challenges and others related to the types of applications discussed above and in other applications. These and other aspects of the present invention are exemplified in a number of illustrated implementations and applications, some of which are shown in the figures and characterized in the claims section that follows.

Various embodiments of the present invention are applicable to a thin-film dielectric material, and approaches to manufacturing and implementing the same. According to an example embodiment of the present invention, an organic thin-film device includes a dielectric layer including an organic polymer cross-linked with a reaction-stabilized polymer-cross-linking material.

According to another example embodiment of the present invention, an organic thin-film capacitive device includes a substrate, an electrode and a dielectric layer arranged between a channel in the substrate and the electrode. The dielectric layer includes an organic polymer cross-linked with a reaction-stabilized polymer-cross-linking material. For certain applications, the organic polymer includes a material such as phenol or hydroxyl.

In some implementations, the capacitive device further includes circuit nodes that are electrically coupled by the channel when an electric field is applied to the channel via the electrode and dielectric layer. Such nodes may include, for example, source and drain electrodes that form part of an organic thin-film transistor (OTFT).

According to another example embodiment of the present invention, a method for manufacturing an organic thin film capacitive device implements a reaction-stabilized material. An organic polymer material is mixed in a solution with a reaction-stabilized polymer-cross-linking material, and the solution is coated on a substrate. After coating, the solution is cured at an elevated temperature to facilitate a reaction to cross-link the organic polymer material with the cross-linking material to form a dielectric layer.

The above summary is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which.

Figure 1:
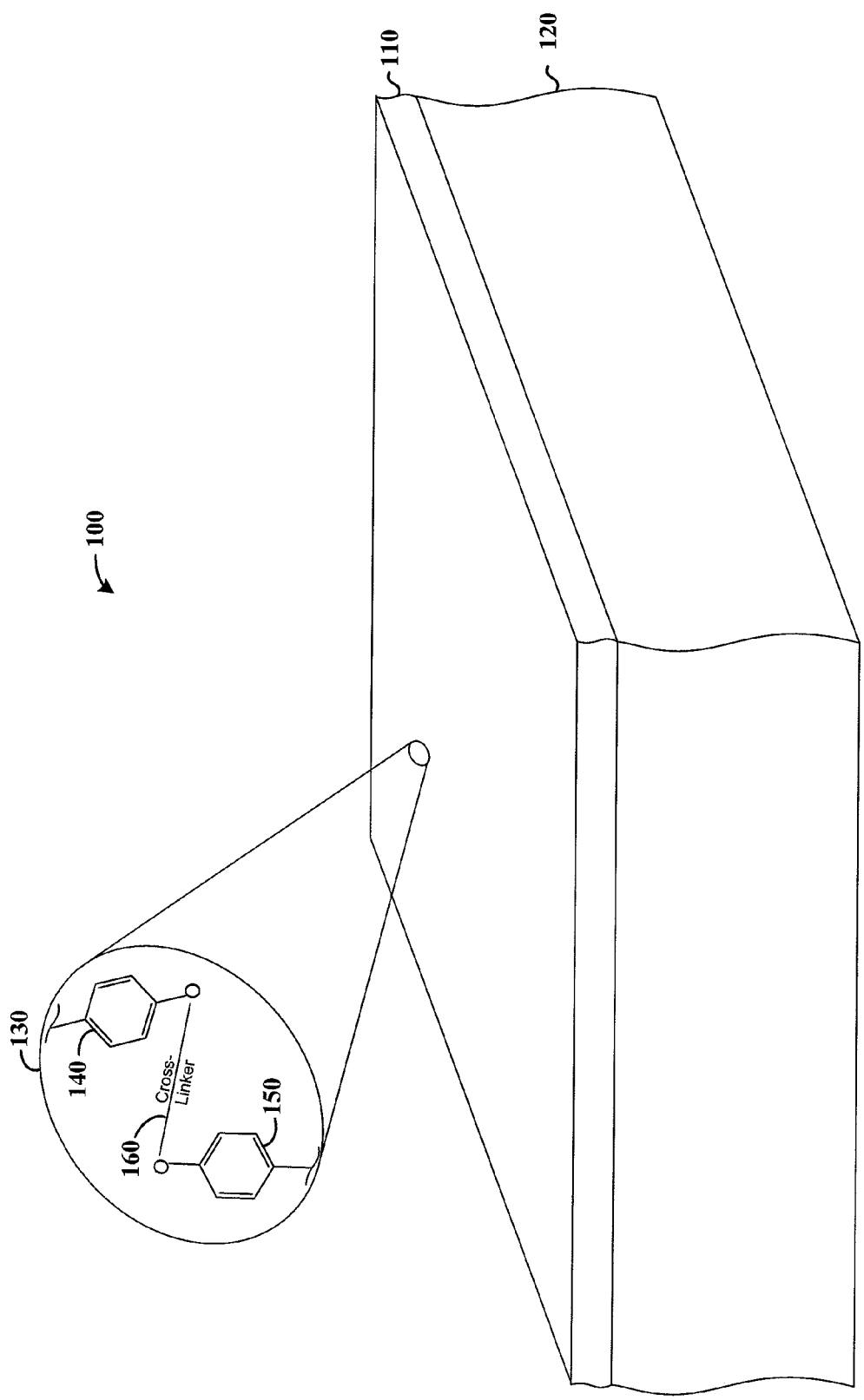
FIG. 1 shows a cross-linked dielectric material formed over a substrate, in accordance with an example embodiment of the present invention.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be applicable to a variety of different types of processes, devices and arrangements involving thin, cross-linked dielectric materials. While the present invention is not necessarily so limited, various aspects of the invention may be appreciated through a discussion of examples using this context.

According to an example embodiment of the present invention, a cross-linked dielectric layer is manufactured using an organic polymer such as a hydroxyl-including or phenol-including polymer (e.g., polyvinyl alcohol or poly(4-vinylphenol) (PVP)) in a cross-linking solution that is reaction-stabilized and amenable to low-temperature cross-linking. The solution includes an organic polymer material and a reaction-stabilized cross-linking material that links the organic polymer material together upon reaction.

In the context of example embodiments described herein, the reaction-stabilized polymer-cross-linking material is a material that is stable with the organic polymer such that a solution containing both the cross-linking material and polymer is reaction-stabilized (e.g., exhibits a low rate of reaction) over an extended time period. That is, the cross-linking material can be maintained in solution with the polymer material for an extended time before applying the solution to form the dielectric layer by reacting the materials to cross-link the polymer. For instance, such a cross-linking material involves, in some applications, a cross-linking material that is stable in that it does not form a polymer with itself. Furthermore, the reaction-stabilized cross-linking material is a material that cross-links with a polymer at an elevated temperature (e.g., greater than room temperature) that is less than about 140° C.

In some applications, a time-stabilized (polymer and cross-linking) solution as discussed above exhibits a polymer/cross-linking rate of reaction that is generally low, facilitating stability of the polymer and cross-linking solution for several hours, days or even weeks. For instance, one type of polymer and cross-linking solution has a rate of reaction such that less than about 10% of an —OH group on the polymer is cross-linked over a time period of one or two days, and in some instances, several days (e.g., about 6 days). In certain applications, a polymer and cross-linking solution exhibits less than about 5% reaction of an —OH group over similar time periods. In other applications, the reaction rate and corresponding time periods are related to the ratio of the polymer to cross-linking material.

In some applications, the reaction-stabilized polymer-cross-linking material is reaction-stabilized with water. In such applications, the reaction-stabilized polymer-cross-linking material is amenable to use in conditions susceptible to water or humidity, such as with an in-solution condition, where the polymer-cross-linking material is exposed to water prior to its use in the formation of a dielectric layer. In some applications, the polymer-cross-linking material is stable in-solution with water, such that less than about 20% of the material reacts with water over a period of about one hour, and in other applications, less than about 5% of the cross-linking material reacts with water in about an hour.

In another embodiment, an organic thin-film transistor (OTFT) is fabricated with a polymer cross-linked dielectric layer, and operates at a low voltage (e.g., at or below about 1 V). In many applications, the low-voltage OTFT is amenable to operation in an environment susceptible to water as discussed above. Such operation is facilitated by, for example, the OTFT's ability to operate at relatively low voltage. Moreover, the OTFT is amenable to operation in water-susceptible conditions without necessarily requiring encapsulation.

According to another example embodiment of the present invention, an OTFT dielectric material includes a PVP polymer with one or more of a variety of cross-linking agents. In some applications, the cross-linking occurs through the formation of an ester bond between a hydroxyl group of a PVP monomer and a reactive group of a small molecule containing at least two reactive groups, such as an acyl chloride, anhydride, carboxylic acid or isocyanate. In some reactions using an anhydride or carboxylic acid, a reaction promoting agent such as a catalytic amount of an organic base is included in a reaction mixture with the PVP monomer and the reactive group.

In connection with one or more approaches as discussed in the previous paragraph, a low-pinhole and/or pinhole-free dielectric layer is formed having a relatively small thickness, and in some applications, having a thickness of about 8 nm. Transistor and other capacitive devices fabricated using a cross-linked PVP dielectric layer as described herein are implemented for low-voltage operation, and in some applications, for operating below 500 mV. As discussed above, such low-voltage operation facilitates operability under water-susceptible conditions, such as with underwater applications involving organic semiconductor molecules.

For some embodiments involving OTFTs, cross-linked dielectric materials such as those discussed above are implemented for sensor applications such as those described in U.S. patent application Ser. No. 11/781,749 (incorporated herein by reference), entitled "Organic Thin-film Transistor Sensor Arrangements" and filed concurrently, which also claims the benefit of the above-referenced Provisional Patent Application to which benefit is claimed herein.

The following example embodiments describe approaches involving a cross-linked PVP dielectric material by way of example. However, some or all of the embodiments are selectively implemented with another polymer material, such as those described above. For instance, a different type of polymer having a phenol group, or a polymer having a hydroxyl group, may be implemented in place of the PVP material as discussed below. In such applications, the cross-linking material is stable, as described above, with the particular polymer material that is implemented (e.g., phenol-containing or hydroxyl-containing polymer material).

Turning now to the Figures, FIG. 1 shows a device 100 with a cross-linked PVP dielectric material 110 formed on a substrate 120, according to another example embodiment of the present invention. The dielectric material 110 is formed from a solution including PVP with cross-linking material, which is arranged on the substrate 120 (e.g., via spin-coating). Inset 130 shows an exemplary representation of a portion of the cross-linked dielectric material 110, with two PVP monomers 140 and 150 linked by a cross-linker material 160.

Upon heating, in some applications to about 60° C., in other applications to about 90° C., and in still other applications to about, or exceeding, 120° C., the PVP material in the solution cross-links via the cross-linking material to form the dielectric material 110. In some applications, the temperature is set high enough to remove solvent from the solution and to cross-link the PVP, yet low enough to facilitate use with a particular material used for the substrate 120 (e.g., where the substrate is polyester, below about 120° C.). The resulting device 100 is useful for a variety of capacitive applications, with a gate or other electrode adjacent the dielectric material.

In certain embodiments, the dielectric material 110 is treated with octadecyltriethoxysilane (OTS). Where implemented in capacitive applications, this treatment facilitates a reduction in leakage current. For transistor applications, the OTS treatment facilitates a relatively high mobility and on/off ratio.

In some applications, the substrate 120 includes a material susceptible to undesirable conditions when heated above a certain temperature (e.g., above 90° C., above 120° C. or above 140° C.). Such materials include, for example, one or more of polyester or PMMA (polymethyl methacrylate). With such materials, the aforesaid cross-linking approach is beneficial in that the cross-linking is carried out at a temperature low enough to suit the needs of the substrate 120.

Similarly, the cross-linking material used to cross-link the PVP material is selected to suit the application and/or from available materials. In some applications, the cross-linking material is from a class of materials including an ester and/or a urethane, such as acyl chloride, anhydride, carboxylic acid and isocyanide. In certain embodiments, the cross-linking material is part of a molecule or arrangement with the PVP material, and cross-links the PVP material, with which it is arranged, to other PVP material.

Figure 2:
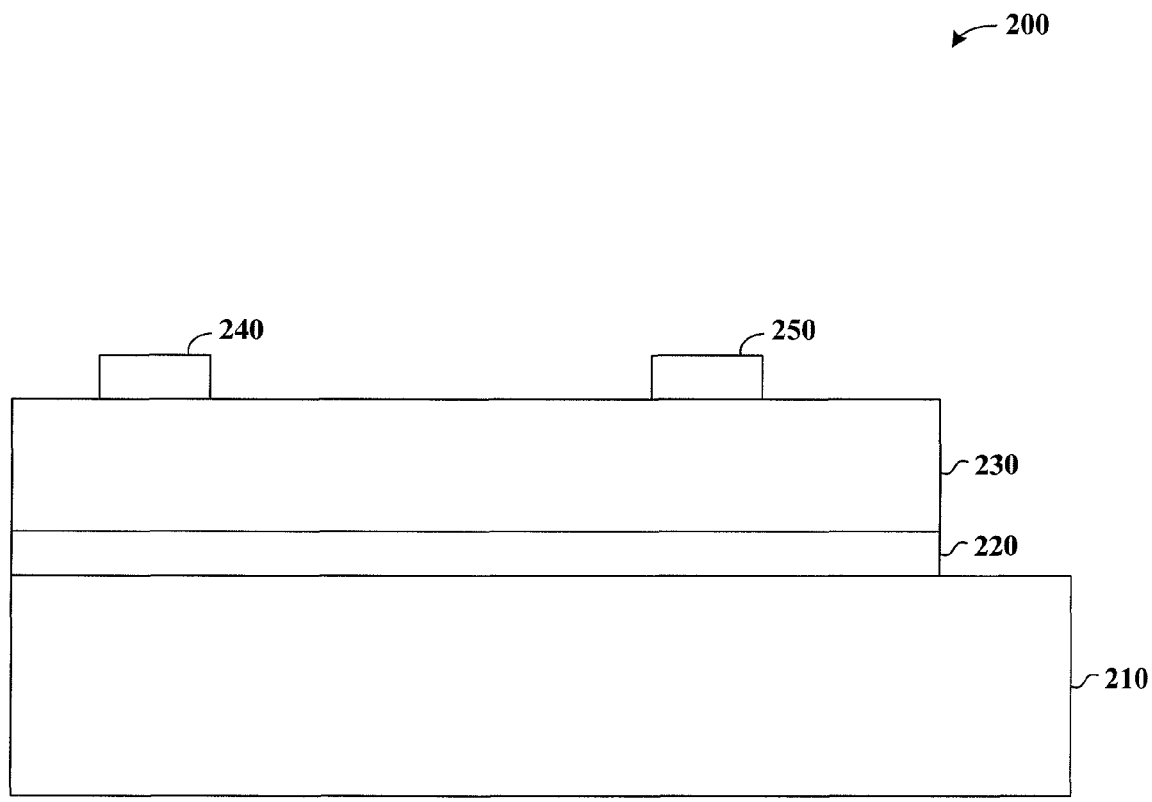
FIG. 2 shows a cross-sectional view of an organic thin-film transistor (OTFT) having a dielectric layer formed in connection with another example embodiment of the present invention.

FIG. 2 is a cross-sectional view of an organic thin-film transistor (OTFT) 200 having a cross-linked PVP dielectric layer, according to another example embodiment of the present invention. The OTFT 200 shown is in a bottom-gate, top contact arrangement; however, various example embodiments are directed to a variety of such OTFTs, in bottom and top gate arrangements, and in bottom and top contact arrangements, as well as other arrangements as appropriate.

The OTFT 200 includes a gate material 210 with a dielectric material 220 on the gate material 210 and having a PVP material cross-linked as described herein. A semiconductor material 230 is over the dielectric material and includes a channel region between source and drain 240 and 250, respectively. The gate material 210 is adapted to bias the channel region via the dielectric material 220 (e.g., at a voltage of less than about 2V, and in some applications, less than about 1 V) to switch the channel region between on (generally high conductivity) and off (generally low conductivity) states for electrically coupling the source and drain 240 and 250.

As discussed herein, the OTFT 200 is amenable to use in conditions susceptible to water exposure, such as in humid conditions or for underwater use (e.g., without necessarily encapsulating the dielectric material or other portion of the OTFT). In some applications, the dielectric material 220, gate 210 and semiconductor material 230 are arranged to operate in conditions susceptible to water, with the gate 210 switching the channel region in the semiconductor material 230 between on and off states to selectively pass current in response to a voltage of less than about 1V applied to the gate.

Figure 3:
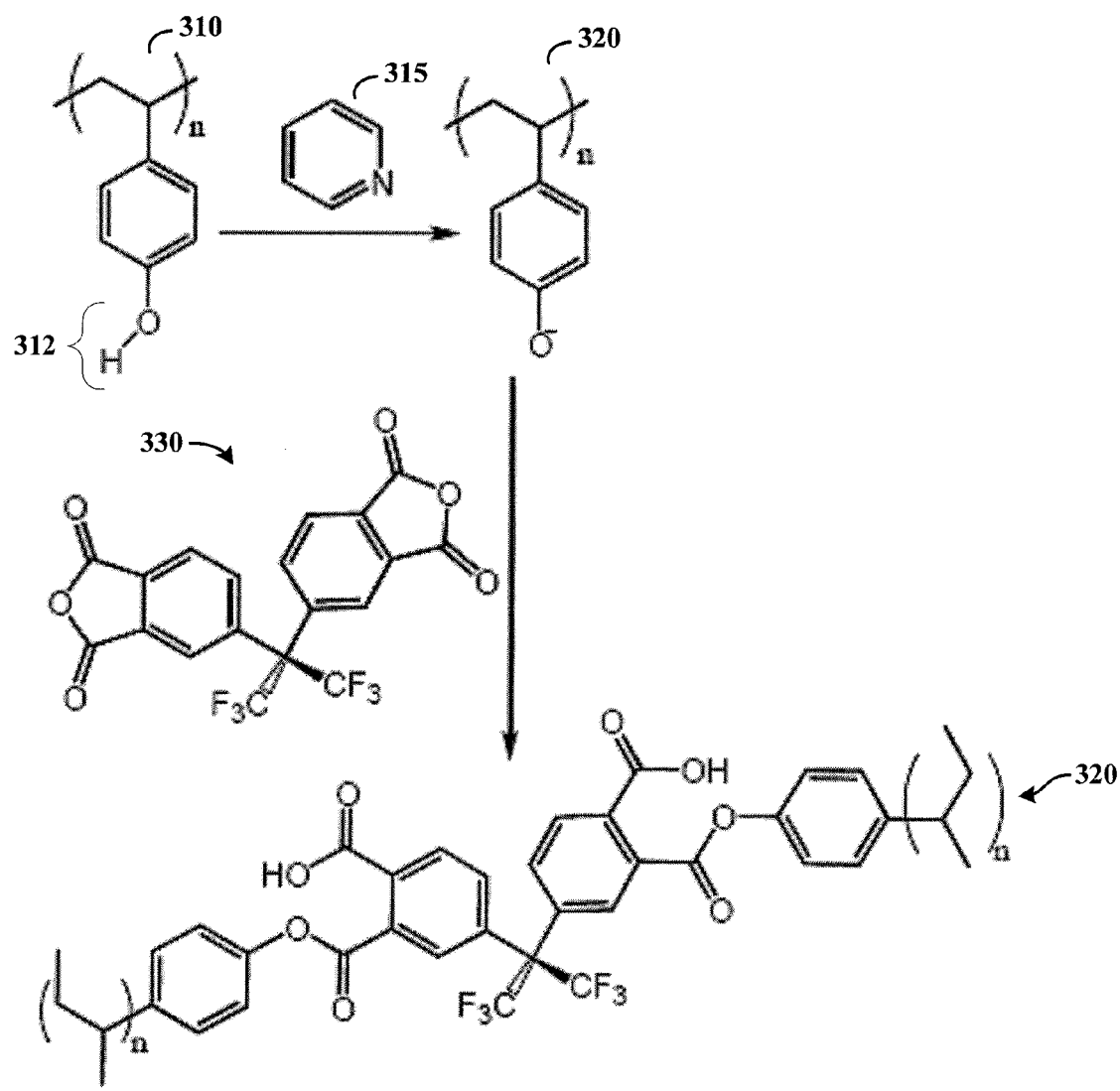
FIG. 3 shows an approach to cross-linking poly(4-vinylphenol) (PVP) in the formation of a dielectric layer, according to another example embodiment of the present invention.

FIG. 3 shows an approach to cross-linking PVP in the formation of a dielectric layer, according to another example embodiment of the present invention. The approach shown in FIG. 3 is applicable to the formation of a multitude of cross-linked materials from a PVP solution (with one linked set of PVP shown by way of example). A PVP monomer 310 is placed in a propylene glycol monomethyl ether acetate (PGMEA) solution with a 4,4'-(Hexafluoroisopropylidene)diphthalic anhydride (HDA) cross-linking material 330 and a pyridine base 315 as a catalyst.

As discussed above, and as described with specific examples below, a variety of cross-linking materials may be used instead of (or, perhaps, in addition to) the HDA cross-linking material 330. Similarly, a variety of catalyst materials (e.g., organic base) may be used instead of and/or in addition to the pyridine base 315. Moreover, in some applications, no catalyst material is used. Similarly, a variety of organic solvents may be used instead of and/or in addition to the propylene glycol monomethyl ether acetate.

In solution, the PVP monomer 310, pyridine base 315 and HDA cross-linking material 330 are applied to a substrate (e.g., spun-on to a substrate), such as the substrate 120 shown in FIG. 1. The substrate is heated at a selected temperature, in some applications to about 90° C. for about 1 hr. The pyridine base 315 facilitates the removal of hydrogen from a hydroxyl group 312 (the result as shown with the PVP monomer 320), with the pyridine base 315 forming a pyridinium cation. The hydroxyl group (now O⁻ via the catalyst) of each of two of the PVP monomers 320 forms an ester bond with anhydride groups of the HDA cross-linking material 330 to foam the cross-linked PVP arrangement 340.

The following describes various approaches to the formation of a dielectric layer on a substrate, in connection with various example embodiments of the present invention. Some of these approaches may be implemented, for example, in forming structures such as that shown in connection with FIG. 1 and/or FIG. 2 above.

Before applying a solution to form a dielectric material, the substrate on which the dielectric material is to be formed is cleaned or otherwise prepared. For instance, the substrate may be cleaned by sonication in isopropyl alcohol for about 5 min., with inorganic substrates subjected to an UV ozone treatment (e.g., about 20 min.), and organic substrates subjected to an oxygen plasma treatment (e.g., 65 Watts, 200 mTorr oxygen for about 2 minutes).

The solution is prepared in a manner commensurate with applicability with the particular cross-linker being used. In applications involving an acyl chloride cross-linker, about 20 mg poly(4-vinylphenol) (PVP) is added per 1 mL solution in propylene glycol monomethyl ether acetate (PGMEA). The solution is briefly sonicated until dissolved. About 4 mg acyl chloride species is added and mixed thoroughly. The solution is optionally filtered through a 2 μm filter.

In applications involving a dianhydride or carboxylic acid cross-linker, about 20 mg PVP is added per 1 mL solution in propylene glycol monomethyl ether acetate, and the solution is briefly sonicated until dissolved. About 2.4 μL triethylamine is added and mixed thoroughly, but lower quantities can be used. About 2 mg of a dianhydride species is added to the solution and evenly mixed. As with the above, the solution is optionally filtered through a 2 μm filter.

Once the solution and substrate have been prepared, a film of the solution is formed on the substrate. If desirable, the substrate is blown clean with filtered compressed air, nitrogen or argon gas. The substrate is evenly coated with the PGMEA solution (e.g., about 40-50 μl, per 1 cm²). After a brief wait (e.g., about 3 sec.), the substrate is held (e.g., using a vacuum chuck to hold the substrate) and spun at 7000 rpm with rapid acceleration. One spin-coating arrangement that can be used in connection with this and other embodiments is the spin-coater available from Headway Research, Inc., set at an acceleration of about 10 for 1 min. This time and acceleration are varied for different applications. After coating, the substrate is cured on a 120° C. hotplate for about 30 min., and placed in a vacuum oven at about 90° C. for about 1 hr. The coating forms a dielectric layer on the substrate (e.g., similar to the dielectric layer 110 in FIG. 1, on substrate 120). In some applications, the thickness of the dielectric layer is increased by repeating the application of a coating to the cured dielectric, and curing the newly-applied coating, one or more times to achieve a desired thickness. Also, the rate of spin, the concentration of polymer solution and other application characteristics may also be modified to achieve different thicknesses.

Once the dielectric layer is formed on the substrate, it is used to make one or more of a variety of capacitive type devices, such as an OTFT as shown in FIG. 2. For transistor fabrication, a cross-linked PVP layer was prepared in a manner commensurate with the above approach, on an n-doped silicon substrate that functions as a gate electrode. Referring to FIG. 2 by way of example (and understanding that the OTFT in FIG. 2 may be implemented with other substrates, dielectrics, arrangements and formation approaches), a dielectric layer 220 is formed on an n-doped silicon substrate 210. In some applications, the dielectric layer is formed to a thickness and composition that facilitates a capacitance per unit area (Ci) ranging between about $0.5-4.0 \cdot 10^{-7}$ $F/cm^2$. A lower capacitance is achievable by increasing the cross-linked dielectric film thickness.

An organic semiconductor such as one of pentacene, perfluorinated copper phthalocyanine, and 5,5'-bis(7-dodecyl-9H-fluoren-2-yl)-2,2'-bithiophene (DDFTTF), is formed on the dielectric layer (e.g., as semiconductor material 230 in FIG. 2) and deposited at a rate of about 0.1-1 Å/s under a pressure of $5.0 \cdot 10^{-7}$ Torr to a final thickness of 100-450 Å. The substrate temperature during deposition is selectively controlled by heating a support for the substrate, such as a copper or other block on which the substrate is mounted.

A top contact geometry is used, with electrodes (e.g., gold) deposited after the semiconductor deposition, using shadow masks with a W/L of 20, where L=50 µM at a deposition rate of 1 Å/s onto a rotating substrate.

Figure 4:
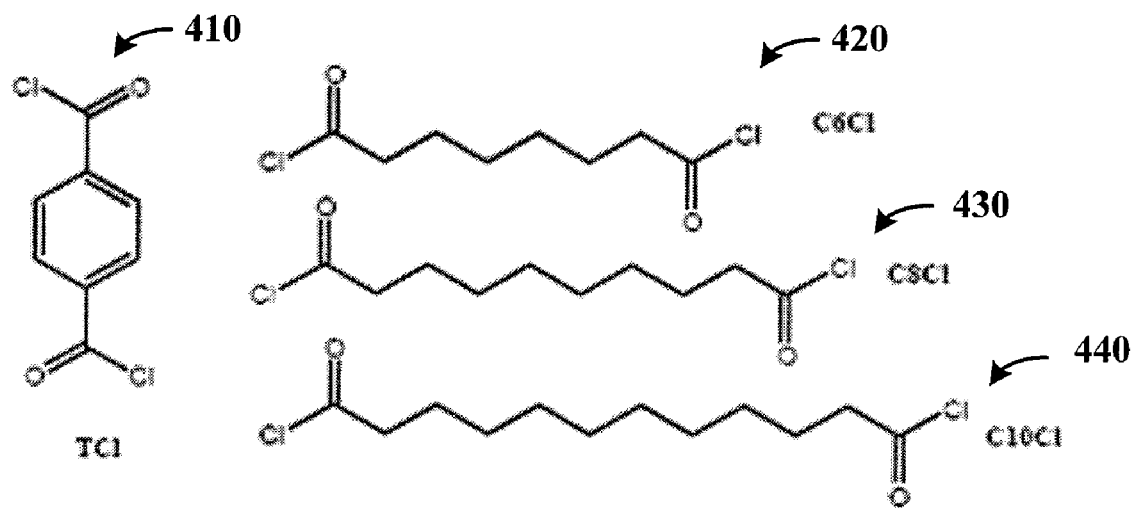
FIG. 4 shows acyl chloride cross-linking agents used in accordance with example embodiments of the present invention.

As discussed above, a variety of cross-linking agents (materials) can be implemented, depending upon the other materials used and availability of cross-linking materials. In some example embodiments, acyl chloride cross-linking agents are used. For instance, FIG. 4 shows acyl chloride cross-linking agents used in accordance with example embodiments of the present invention, with the cross-linking agents shown as follows: agent 410 is Terephthaloyl chloride (TCl); agent 420 is octanedioyl dichloride (C6Cl); agent 430 is decanedioyl dichloride (C8Cl); and agent 440 is dodecanedioyl dichloride (C10Cl).

Generally, acyl chloride cross-linking materials are not limited to diacyl dichlorides, and in some applications are extended to 3 or more reactive acyl chloride groups. In some applications, the core molecule includes a species other than linear alkyl or aromatic species, such as branched and mixed alkyl and aromatic or three-dimensional structures. In addition, the core molecule is not limited to organic species, and may be extended to inorganic systems, including high dielectric constant nanoparticles such as $Al_2O_3$ or $TiO_2$.

Figure 5:
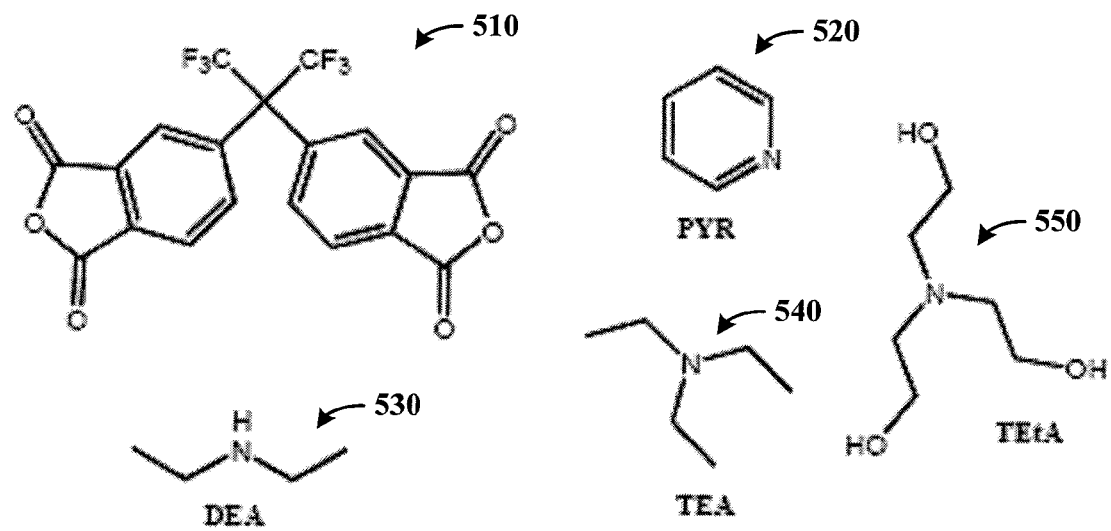
FIG. 5 shows a dianhydride cross-linking agent and various catalyst bases used in accordance with example embodiments of the present invention.

In another example embodiment, dianhydride cross-linking agents are used to link PVP material for a dielectric layer. For example, FIG. 5 shows a dianhydride cross-linking agent and various catalyst bases used in accordance with example embodiments of the present invention, shown as follows: agent 510 is 4,4'-(Hexafluoroisopropylidene)diphthalic anhydride (HDA); catalyst base 520 is Pyridine (PYR); catalyst base 530 is Diethylamine (DEA); catalyst base 540 is Triethylamine (TEA); and catalyst base 550 is Triethanolamine (TEtA). Other catalyst bases such as Dimethylaminopyridine (DMAP) may also be used.

In some embodiments involving TEA, a sample is placed in a closed environment with a spun PVP/HDA film and HDA vapor to mitigate undesirable conditions relating to the use of TEA in solution. In some applications, the TEA is heated to about 80° C. and the sample is left in the closed environment for about 30 min. In other applications, Nitrogen gas is used to flow TEA vapor onto substances during a film anneal step.

Films used in connection with various embodiments are formed and implemented in a variety of manners involving sonication. In some applications, a PVP film is sonicated in tetrahydrofuran (THF) to remove a substantial portion of the film (e.g., 95% of the thickness of the film) to form a thin or ultra-thin dielectric (e.g., with sonication for about 5 min.). In other applications, a PVP/TCL cross-linked layer is sonicated to remove about 20-30% of the thickness of the film (e.g., also with about 5 min. of sonication).

In still other applications, a PVP/HDA cross-linked layer is sonicated in THF (e.g., for about 10 min.) to remove a small portion of the layer, such as about 1% or less of the thickness of the layer to produce a stable film in ambient and non-dry solvent conditions (e.g., anhydride). In some implementations, the PVP-HDA cross-linked layer is base catalyzed to facilitate reaction.

In addition to the above, various other bases or reaction promoters are selectively used in various amounts to catalyze the cross-linking reaction, in connection with a HDA cross-linking agent, other dianhydride cross-linking agent, or other cross-linking agents. Moreover, anhydride cross-linking materials are not limited to two reactive groups, and may be extended to three or more reactive anhydride groups, depending upon the application. For instance, dianhydride species may be extended to linear or branched alkanes. Core molecules may be linear or aromatic, or any combinations thereof, and are not limited to organic species, but may be extended to inorganic systems, including nanoparticles.

Figure 6:
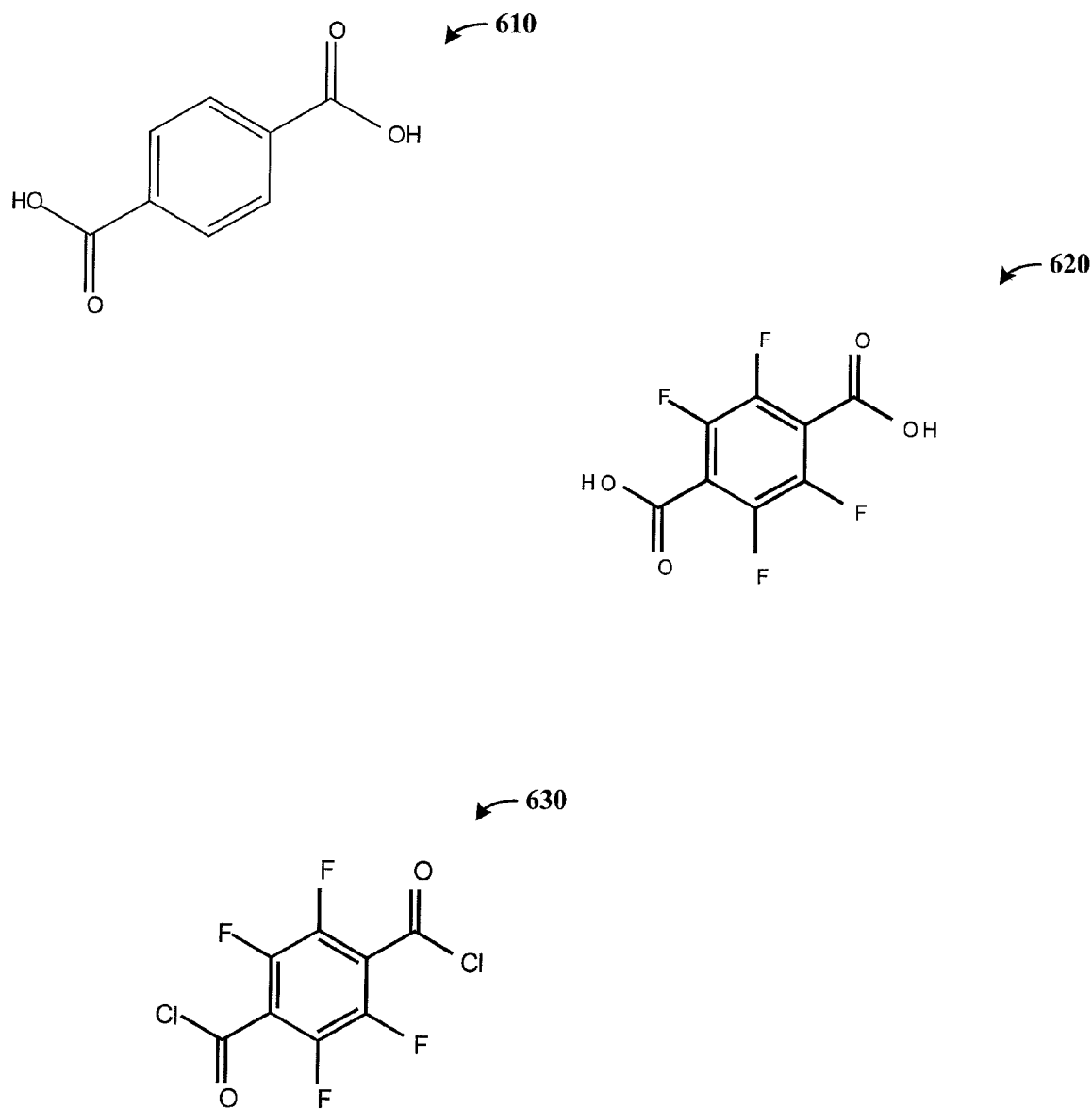
FIG. 6 shows cross-linking agents used in connection with other example embodiments of the present invention.

Carboxylic acids are another type of cross-linking agent used in connection with other example embodiments. For instance, FIG. 6 shows example carboxylic acids including terephthalic acid (TA) 610 and tetrafluoroterephthalic acid (FTA) 620. Another cross-linking agent shown in FIG. 6 is tetrafluoroterephthaloyl chloride 630 which is formed, for example, from FTA (using $SOCl_2$ and $CH_2Cl_2$).

In some applications involving carboxylic acids, various bases or reaction promoters, such as those mentioned above, are used to facilitate the cross-linking reaction between carboxylic acids and the PVP polymer. Carboxylic acid cross-linkers are not limited to two reactive groups, and in some applications, include three or more reactive carboxylic acid groups. In some applications, carboxylic acid core molecular species include linear or branched alkanes, linear or aromatic, or any combinations thereof. Moreover, the core molecular species may be organic as discussed, or involve inorganic systems, and may include nanoparticles.

According to another example embodiment of the present invention, isocyanate cross-linking agents are used to form a cross-linked dielectric. In some applications, the isocyanate agent includes more than one reaction species per molecule. Certain applications are directed to isocyanates having a polymer or small molecule species, and certain applications employ inorganic or organic molecules.

In connection with another example embodiment, a polyvinylphenol co-polymer/alt-polymer cross-linking agent is used to form a crossed-linked dielectric. In some applications, a co-polymer or alternating polymer including PVP and a cross-linking agent, such as anhydride (e.g., from maleic anhydride or another anhydride containing monomer) is incorporated in a similar manner as described above in connection with the dianhydride discussion. In other applications, the co-polymer/alt-polymer includes polyvinylphenol or any other cross-linking agent described herein.

In connection with one or more of the above examples, a variety of solvents are used in making the solutions in which a cross-linking material is mixed with PVP and, as appropriate, other materials. Solvents applicable for use in connection with various example embodiments include propylene glycol monomethyl ether acetate (PGMEA), tetrahydrofuran (THF), isopropanyl alcohol (IPA) and tert-butyl alcohol (TbOH).

Table 1 on the following page characterizes various cross-linked layers as formed in accordance with various example embodiments, with columns indicating cross-linker, PVP and CL amounts, solvent type, base (if applicable), spin rate (of the layer) and cure temperature, respectively.

TABLE 1

| (CL) | PVP mg/mL | CL mg/mL | solvent | base, eq | spin rate (RPM) | Temp (° C.) |
|---|---|---|---|---|---|---|
| C6CI | 20 | 4 | PGMEA | — | 4K, 5K, 7K, 9K | 150 |
| C6CI | 20 | 4 | PGMEA | — | 4K, 5K, 7K, 9K | 120 |
| C6CI | 20 | 4 | PGMEA | — | 5K | 90 |
| C6CI | 20 | 4 | PGMEA | — | 5K | 60 |
| C6CI | 30 | 6 | PGMEA | — | 4K, 5K, 7K, 9K | 150 |
| C6CI | 10 | 2 | PGMEA | — | 4K, 5K, 7K, 9K | 150 |
| C8CI | 10 | 2 | PGMEA | — | 4K, 5K, 7K, 9K | 150 |
| C10CI | 10 | 2 | PGMEA | — | 4K, 5K, 7K, 9K | 150 |
| C6CI | 10 | 4 | PGMEA | — | 3K, 5K, 7K | 150 |
| C8CI | 10 | 4 | PGMEA | — | 3K, 5K, 7K | 150 |
| C10CI | 10 | 4 | PGMEA | — | 3K, 5K, 7K | 150 |
| C6CI | 10 | 10 | PGMEA | — | 3K, 5K, 7K | 150 |
| C8CI | 10 | 10 | PGMEA | — | 3K, 5K, 7K | 150 |
| C10CI | 10 | 10 | PGMEA | — | 3K, 5K, 7K | 150 |
| C6CI | 10 | 20 | PGMEA | — | 3K, 5K, 7K | 150 |
| C8CI | 10 | 20 | PGMEA | — | 3K, 5K, 7K | 150 |
| C10CI | 10 | 20 | PGMEA | — | 3K, 5K, 7K | 150 |
| C6CI | 10 | 20 | THF | — | 3K, 5K, 7K | 150 |
| C8CI | 10 | 20 | THF | — | 3K, 5K, 7K | 150 |
| C10CI | 10 | 20 | THF | — | 3K, 5K, 7K | 150 |
| C6CI | 10 | 10 | IPA | — | 3K, 5K, 7K | 150 |
| C8CI | 10 | 10 | IPA | — | 3K, 5K, 7K | 150 |
| C10CI | 10 | 10 | IPA | — | 3K, 5K, 7K | 150 |
| HDA | 20 | 2 | PGMEA | TEA, 0.05 | 4K, 5K, 7K, 9K | 90 |
| HDA | 20 | 4 | PGMEA | TEA, 0.05 | 4K, 5K, 7K, 9K | 90 |
| HDA | 10 | 1 | PGMEA | TEA, 0.05 | 4K, 5K, 7K, 9K | 150 |
| HDA | 10 | 1 | PGMEA | TEA, 0.05 | 4K, 5K, 7K, 9K | 120 |
| HDA | 10 | 2 | PGMEA | TEA, 0.05 | 4K, 5K, 7K, 9K | 150 |
| HDA | 10 | 5 | PGMEA | TEA, 0.05 | 4K, 5K, 7K, 9K | 150 |
| HDA | 10 | 10 | PGMEA | TEA, 0.05 | 4K, 5K, 7K, 9K | 150 |
| HDA | 10 | 10 | PGMEA | TEA, 0.01 | 4K, 5K, 7K, 9K | 150 |
| HDA | 10 | 10 | PGMEA | TEA, 0.1 | 4K, 5K, 7K, 9K | 150 |
| HDA | 10 | 2 | PGMEA | DEA, 0.05 | 4K, 5K, 7K, 9K | 150 |
| HDA | 10 | 2 | PGMEA | TEtA, 0.05 | 4K, 5K, 7K, 9K | 150 |
| HDA | 10 | 2 | PGMEA | PYR, 60 | 4K, 5K, 7K, 9K | 150 |
| HDA | 10 | 10 | THF | TEA, 0.05 | 4K, 5K, 7K, 9K | 150 |
| HDA | 10 | 1 | THF | TEA, 0.05 | 4K, 5K, 7K, 9K | 150 |
| HDA | 10 | 10 | THF | PYR, 60 | 4K, 5K, 7K, 9K | 150 |
| HDA | 10 | 10 | IPA | TEA, 0.05 | 4K, 5K, 7K, 9K | 150 |
| HDA | 10 | 10 | TbOH | TEA, 0.05 | 4K, 5K, 7K, 9K | 150 |
| TCI | 5 | 10 | THF | — | 3K | 90 |
| TA | 5 | 10 | THF | — | 3K | 90 |
| FTA | 5 | 10 | THF | — | 3K | 90 |
| TCI | 10 | 20 | THF | — | 3K | 90 |
| TA | 10 | 20 | THF | — | 3K | 90 |
| FTA | 10 | 20 | THF | — | 3K | 90 |
| TCI | 10 | 20 | THF | — | 3K, 5K, 7K | 120 |
| TA | 10 | 20 | THF | — | 3K, 5K, 7K | 120 |
| FTA | 10 | 20 | THF | — | 3K, 5K, 7K | 120 |
| TA | 10 | 20 | THF | PYR, 60 | 3K, 5K, 7K | 120 |
| TA | 10 | 20 | THF | TEA, 0.05 | 3K, 5K, 7K | 120 |

While the present invention has been described above and in the claims that follow, those skilled in the art will recognize that many changes may be made thereto without departing from the spirit and scope of the present invention. Such changes may include, for example, interchanging materials, such as using other Esters or Urethanes as cross-linking materials, or using other PVP-type materials in the dielectric layers. In addition, the thin films and approaches described herein are selectively implemented with one or more of a variety of devices and/or systems, such as capacitors, thin-film and other transistors, optical devices, other semiconductor applications and devices or systems implemented for one or both if organic and inorganic applications. Other applications are directed to those characterized in the above-referenced provisional patent application (and the appendices that form a portion of the provisional patent application) to which benefit is claimed and which is further incorporated herein by reference. Moreover, one or more of the approaches and/or devices herein are implemented for use with applications such as those described and/or referenced by Yoon, M-H., Yan, H., Facchetti, A. and Marks, T. J., in *Low-Voltage Organic Field-Effect Transistors and Inverters Enabled by Ultrathin Cross-Linked Polymers as Gate Dielectrics*, J. Am. Chem. Soc., 2005, 127, 10388-10395, which is fully incorporated herein by reference. These and other approaches as described in the contemplated claims below characterize aspects of the present invention.

What is claimed is:

1. An organic thin-film capacitive device comprising:
   a substrate including a channel region;
   an electrode;
   a dielectric layer electrically arranged between the channel region and the electrode, the dielectric layer including an organic polymer material having a poly(4-vinylphenol) (PVP) based polymer cross-linked with a reaction-stabilized polymer-cross-linking material configured to cross-link with less than about 10% of the polymer in solution over a period of about 24 hours at room temperature, and to cross-link the majority of the organic polymer upon heating to a temperature of between about 60 and 160 degrees Celsius.

2. The device of claim 1, wherein the reaction-stabilized polymer-cross-linking material is a material that, relative to the organic polymer material, is stable at room temperature and cross-links with the organic polymer material at a temperature that is between about 60 and 100 degrees Celsius.

3. The device of claim 1, wherein the reaction-stabilized polymer-cross-linking material is a material that, relative to the organic polymer material, is stable at room temperature and cross-links with the organic polymer material at a temperature that is between about 60° C. and 90° C.

4. The device of claim 1, wherein the reaction-stabilized polymer-cross-linking material is a material that, relative to an organic polymer material, is stable at room temperature and cross-links with the organic polymer material at a temperature that is between about 100° C. and 160° C.

5. The device of claim 1, wherein the reaction-stabilized polymer-cross-linking material includes at least one of an ester and a urethane.

6. The device of claim 1, further including circuit nodes separated by the channel region, wherein the electrode and dielectric layer switch the channel region to electrically couple the circuit nodes in response to a voltage of less than about 2 V applied to the electrode.

7. The device of claim 1, further including circuit nodes separated by the channel region, and wherein, under conditions that expose the dielectric layer to water, the electrode and dielectric layer switch the channel region to electrically couple the circuit nodes in response to a voltage of less than about 2 V applied to the electrode.

8. The device of claim 1, further including circuit nodes separated by the channel region, wherein
the substrate includes a polymer, and
the electrode and dielectric layer switch the channel region to electrically couple the circuit nodes in response to a voltage of less than about 2 V applied to the electrode.

9. The device of claim 1, wherein the reaction-stabilized polymer-cross-linking material is a material that is stable in solution with water.

10. The device of claim 1, wherein the reaction-stabilized polymer-cross-linking material is a material that reacts with water at a rate that is less than about 10% over a period of about one hour.

11. The device of claim 1, wherein the organic polymer material further includes an alcohol-containing polymer.

12. The device of claim 1, wherein the organic polymer material further includes at least another material.

13. The device of claim 1, wherein the polymer-cross-linking material includes a non-polymer material.

14. The device of claim 1, wherein the polymer-cross-linking material is part of a molecular arrangement with the PVP.

15. The device of claim 1, wherein the reaction-stabilized polymer-cross-linking material is configured to,
when in the presence of a cross-linking inhibiting solvent in the solution, cross-link with less than about 10% of the polymer in solution over a period of about 24 hours at room temperature, and
cross-link the majority of the organic polymer upon heating to a temperature of between about 60 and 160 degrees Celsius to remove the solvent.

16. An organic thin-film capacitive device comprising:
a substrate including a channel region that separates circuit nodes, the substrate being susceptible to degradation upon heating to temperatures in excess of about 100 degrees Celsius;
a dielectric layer adjacent the channel region and including an organic polymer cross-linked with a reaction-stabilized polymer-cross-linking material, the reaction-stabilized cross-linking material being
stable in solution with the organic polymer for a period of at least 24 hours at room temperature, during which period the cross-linking material cross-links with less than about 10% of an —OH group on the organic polymer, and
configured to cross-link the organic polymer in response to heating to a temperature of less than about 100 degrees Celsius; and
an electrode adjacent the dielectric layer and configured, in response to the application of a voltage of less than about 2V thereto, to apply an electric field to the channel region via the dielectric layer and effect the creation of a conductive channel in the channel region that electrically connects the circuit nodes.

17. The device of claim 16, wherein the polymer-cross-linking material is configured to exhibit stability to water such that less than about 5% of the cross-linking material reacts with water over a time period of about one hour.

18. The device of claim 16, wherein the organic polymer is PVP.

19. A solution for forming a dielectric layer of an organic semiconductor device, the solution comprising:
an organic polymer including PVP;
a solvent;
a reaction-stabilized polymer-cross-linking material configured, with the solvent, to remain stable with the organic polymer in a solution for a period of at least 24 hours, using the solvent to limit cross-linking with less than about 10% of the organic polymer over the 24-hour period at room temperature, and configured to cross-link the majority of the organic polymer upon heating to a temperature of between about 60 and 160 degrees Celsius.

* * * * *